United States Patent [19]

Brisken

[11] Patent Number: 4,530,363
[45] Date of Patent: Jul. 23, 1985

[54] TRANSDUCER ARRAY FOR SECTOR SCAN AND DOPPLER FLOW MEASUREMENT APPLICATIONS

[75] Inventor: Axel F. Brisken, Shingle Springs, Calif.

[73] Assignee: General Electric Company, Rancho Cordova, Calif.

[21] Appl. No.: 543,945

[22] Filed: Oct. 20, 1983

[51] Int. Cl.³ ............................................. A61B 10/00
[52] U.S. Cl. .................................................... 128/663
[58] Field of Search .................. 128/660, 663; 73/626, 73/861.25

[56] References Cited

U.S. PATENT DOCUMENTS

| | | | |
|---|---|---|---|
| 3,888,238 | 6/1975 | Meindl | 128/660 |
| 4,067,236 | 1/1978 | Hottinger | 128/660 |
| 4,219,846 | 8/1980 | Auphan | 73/626 |
| 4,235,111 | 11/1980 | Hassler | 73/626 |
| 4,242,912 | 1/1981 | Burckhardt | 73/626 |
| 4,307,613 | 12/1981 | Fox | 73/626 |
| 4,422,332 | 12/1983 | Dubuis et al. | 128/660 |

OTHER PUBLICATIONS

Hottinger and Meindl, "Blood Flow Measurements Using the Attenuation Compensated Volume Flow Meter", *Ultrasonic Imaging*, vol. 1, No. 1, 1979.

Fu et al., "Near Field Uniform Beams for Pulsed Doppler Ultrasound", *Ultrasonic Imaging*, vol. 2, 1980, pp. 324–337.

Dretz et al., "Expanded Aperture Annular Array", *Ultrasonic Imaging*, vol. 1, 1979, pp. 56–75.

*Primary Examiner*—Kyle L. Howell
*Assistant Examiner*—Francis J. Jaworski
*Attorney, Agent, or Firm*—Flehr, Hohbach, Test, Albritton & Herbert

[57] ABSTRACT

An array of transducer elements which can be selectively actuated as a linear array for sector scanning and selectively actuated as a plurality of concentric annular arrays for focused Doppler blood flow measurements.

1 Claim, 10 Drawing Figures

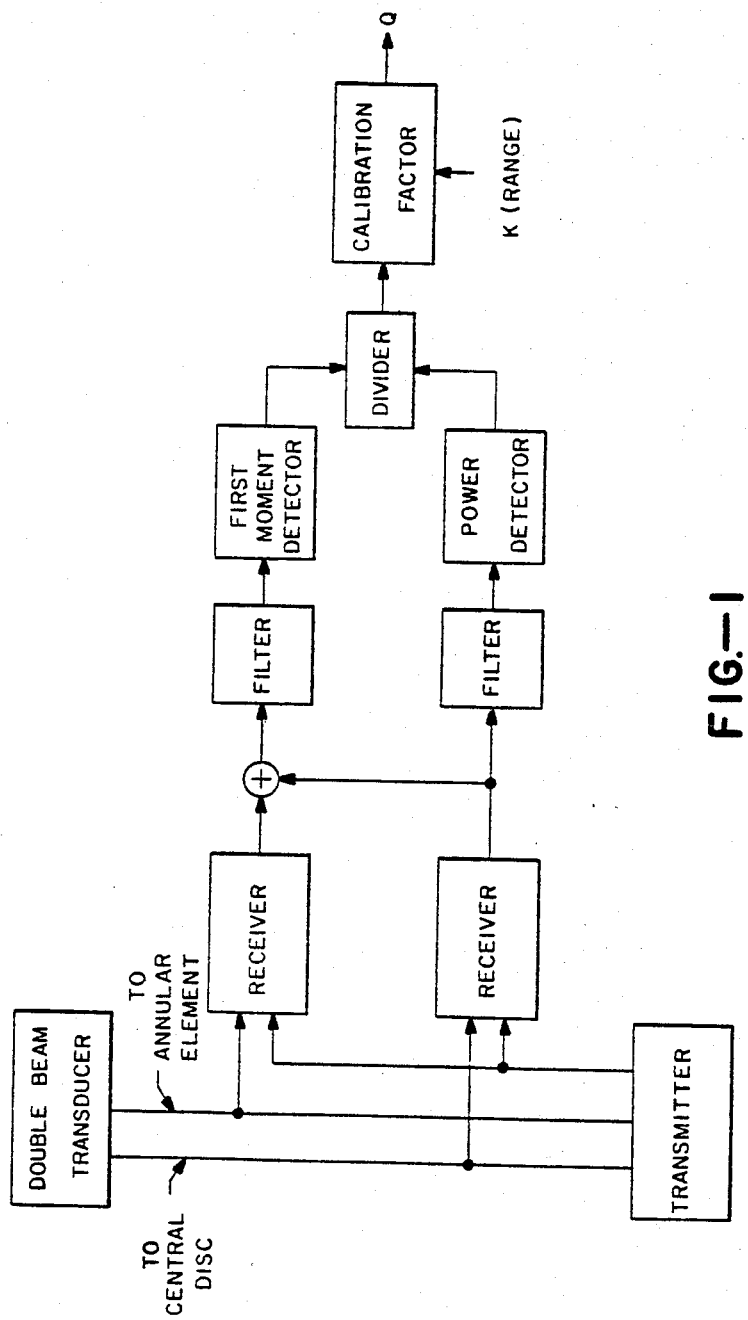
FIG.—1

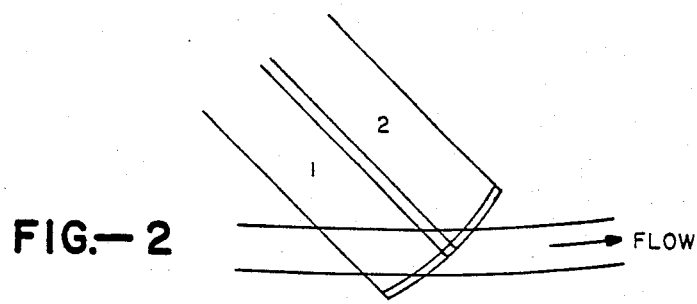
FIG.— 2
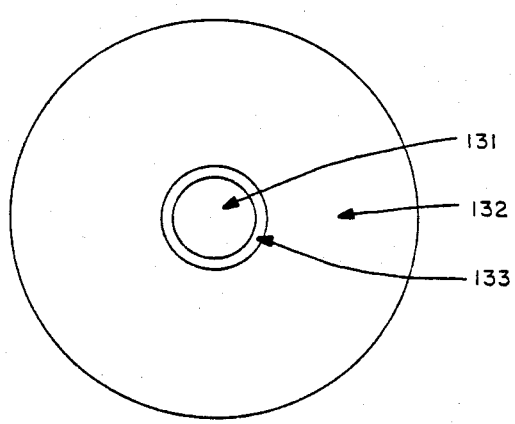
FIG.— 3
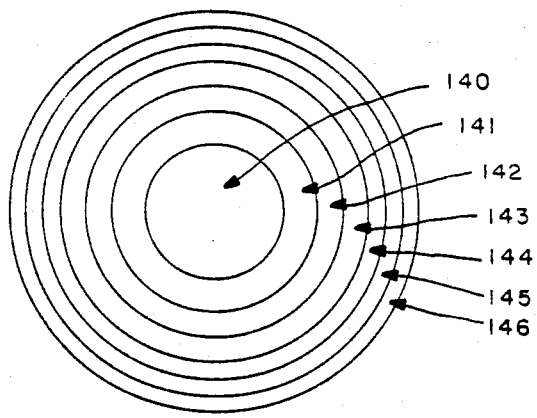
FIG.— 4

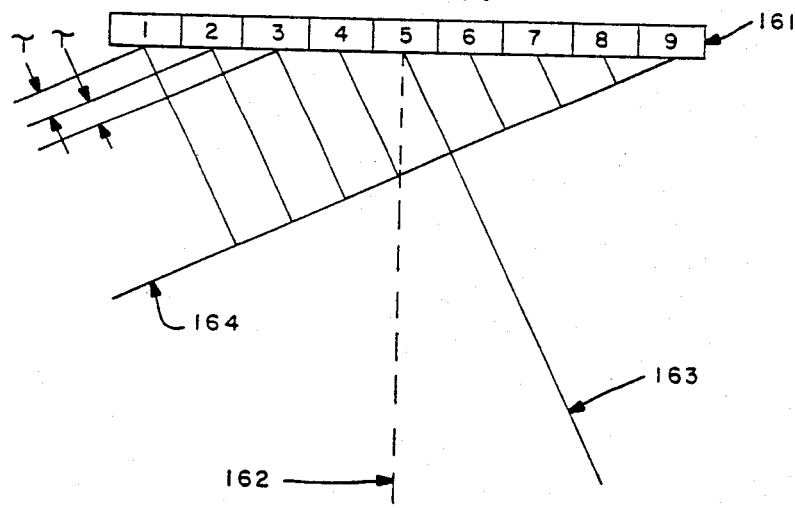
FIG.—6A
FIG.—6B

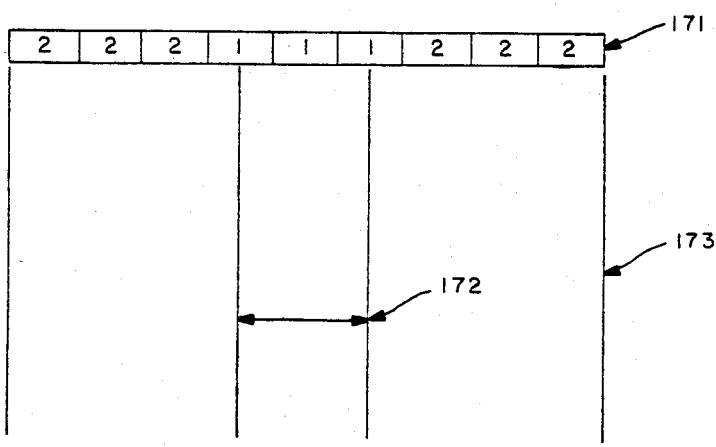
FIG.—7A
FIG.—7B

TRANSDUCER ARRAY FOR SECTOR SCAN AND DOPPLER FLOW MEASUREMENT APPLICATIONS

This invention relates generally to ultrasonic transducers, and more particularly the invention relates to an ultrasonic transducer array which can be employed for sector scan applications and for measuring Doppler blood volume flow in vessels at different depths in a patient.

Doppler ultrasound has been recognized as a potential approach to the non-invasive measurement of blood flow. However, this method has not become a quantitative clinical tool because existing Doppler instruments estimate volume flow as a product of the velocity of blood, the vessel cross sectional area and the cosine of the angle between the Doppler beam and the vessel. This requires accurate measurement of the three-dimensional velocity vector orientation with respect to the ultrasonic beam plus an independent measurement of lumen cross sectional area. Difficulties associated with the accurate determination of these variables have heretofore restricted all non-invasive applications of Doppler flow meters to qualitative measurements.

A novel concept for quantitative non-invasive Doppler blood flow measurement is disclosed by Hottinger and Meindl in "Blood Flow Measurement Using the Attenuation-Compensated Volume Flow Meter" *Ultrasound Imaging*, Vol. 1, No. 1, 1979.

See U.S. Pat. No. 3,888,238 for "Blood Flow Measuring Apparatus". This concept is based on a direct flow-rate estimation rather than on separate velocity, cross sectional area and Doppler angle measurements and does not require precise knowledge of these parameters. The method does require a uniform ultrasonic illumination of the vascular lumen cross section and the positioning of a second small sampling beam inside the vessel. Thus, ultrasonic transducers are required for uniform illumination of the entire vessel cross sectional area and simultaneous focused illumination with range and beam width control.

Heretofore concepts for ultrasonic transducers for realizing the requisite ultrasonic beam patterns have included far-field, near-field and lens approaches. In the far-field approach, the uniform field across the vascular lumen is provided by a diverging beam from the small central disc of an annular array transducer while the focussed sampling beam is provided by the entire aperture. The near-field approach utilizes a transducer composed of two co-planar elements comprising a small central element and a large circumferential element. The two elements are driven simultaneously and equally to simulate a single transducer and thus provide a uniform insonification. In the receive mode, the small element receives a signal from the reference sample volume while the signals received by both elements are summed to collect the signal returning from the whole vessel cross section. In a lens approach a diverging lens is positioned over a small central transducer element to generate a diverging beam that is uniform over a specified solid angle, and a converging lens is placed over an annular element to produce a converging beam.

Researchers at Stanford University have developed a blood flow system which employs a large aperture transducer structure including a central disc and an annular element surrounding the central disc. This near-field approach is described by Fu et al in "Near-Field Uniform Beams for Pulsed Doppler Ultrasound", *Ultrasonic Imaging*, Vol. 2, 1980, pgs. 324–337.

The series limitation from near-field transducers lies in the short depth of focus, starting at the surface of the transducer and ending at typically one to two transducer diameters in the body, depending on transducer frequency. Further, use of these transducer structures assumes that location of an anatomical region or blood vessel of interest is known.

The present invention is directed to a transducer array which can provide a scanning function for location of anatomical regions of interest and which can then function as a variably focused annular transducer array thereby permitting Doppler flow measurements in either shallow blood vessels or in deeper blood vessels.

Accordingly, an object of the invention is a transducer array which can be operated in a sector scan mode and in a focused or unfocused mode.

Another object of the invention is a focused transducer array which has a widely variable focal length.

A feature of the invention is a two-dimensional array of transducer elements which can be selectively energized for providing a sector scan and which can be selectively energized to function as an annular transducer array.

The invention and objects and features thereof will be more readily apparent from the following detailed description and appended claims when taken with the drawing, in which:

FIG. 1 is a functional block diagram of a quantitative Doppler flow meter.

FIG. 2 illustrates requisite ultrasonic beams of transducers using the Hottinger-Meindl method of blood flow measurement.

FIG. 3 depicts a two element annular array per the near-field approach.

FIG. 4 depicts a multi-element annular array.

FIG. 6 is a plan view of the transducer array of FIG. 5 illustrating application thereof in a sector scan modality.

FIG. 7 is a plan view of a transducer array of FIG. 5 illustrating application thereof for near field focusing.

Figures 5, 8:
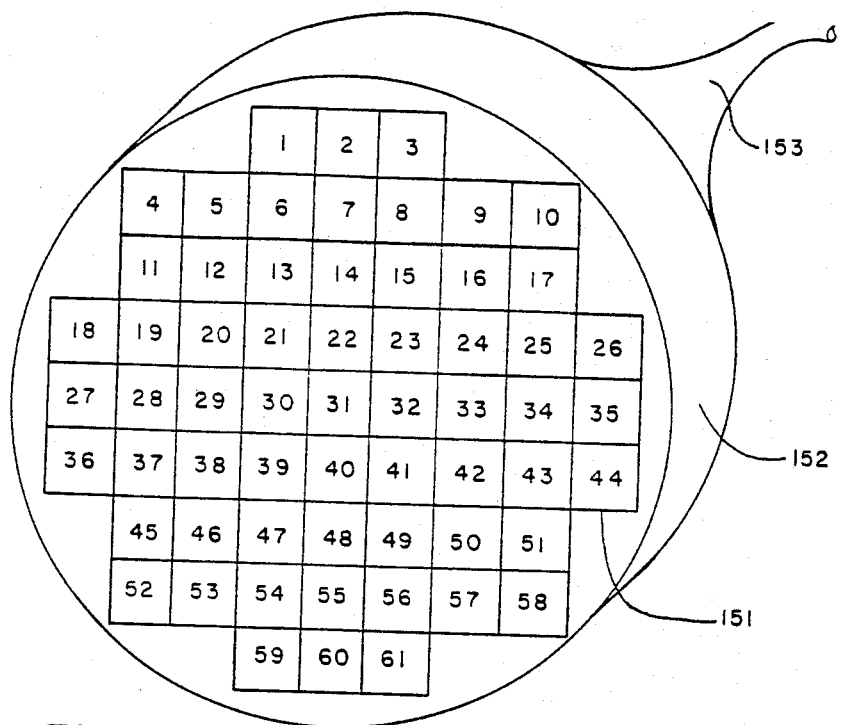
FIG. 5 is a perspective view of an ultrasonic transducer array in accordance with the present invention.
FIG. 8 is a plan view of the transducer array of FIG. 5 illustrating application thereof for far field focusing.

Referring now to the drawings, FIG. 1 is a functional block diagram of the attenuation-compensated volume flow meter as described by Hottinger and Meindl, supra. The flow meter employs a near-field double beam pulsed Doppler transducer which uniformly illuminates a vessel. The array generates repeated short bursts of ultrasound, and the signals returning to the transducer are simultaneously range gated and processed to create two thin sample volumes, as illustrated in the drawing of FIG. 2 which illustrates the waves intersecting a vessel. As shown in FIG. 2, volume 1 constitutes a large uniformly illuminated sample plane covering the entire lumen cross section of the vessel. The second volume is a small disc which is a part of the larger plane and lies totally within the lumen.

As described by Hottinger and Meindl, the two Doppler signals are produced by the transmitter and receiver circuitry of FIG. 1. The received signals pass through filters and to first-moment and power estimator circuits. The flow rate Q at the output is expressed in terms of volume per time and is given as the product of the range dependent scale factor (K) and the Doppler first moment spectrum (derived from the entire transducer surface) and divided by the Doppler power spectrum (derived only from the central disc).

As above described, known transducer arrays for use in Doppler blood flow measurements have limited focusing ability and have currently only been fabricated for blood flow measurements in vessels located near the surface. Further, use of such transducers assumes that the location of the blood vessel is known.

The transducer implemented by Fu et al, supra, is shown in FIG. 3. It consists of a central disc 131 and an outer annular element 132 with an insulation (now radiating) gap 133 between these two. The central disc is designed to have a cross section less than the vascular lumen under clinical investigation. FIG. 4 depicts a multielement annular array known to the literature and specifically defined by Dietz et al in "Expanded Aperture Annular Array", *Ultrasonic Imaging,* Vol. 1, 1979, pgs. 56–75. It is readily apparent that the multielement annular array can function in the same manner as the array of Fu et al, with added benefit of allowing dynamic focus. In FIG. 4, 140 represents the central disk and 141 to 146 the annular rings, in ascending order. FIG. 4 does not detail the interelement gaps.

In accordance with the present invention a transducer array is provided which can be used in both the sector scan mode of operation and in a variably focused Doppler flow measurement application. FIG. 5 is a perspective view of one embodiment of a transducer array in accordance with the invention. A plurality of piezoelectric transducer elements 151 (typically 61 in number) are arranged on the surface of a support member 152 with each transducer element being electrically and acoustically isolated from each other. Each transducer element has a conductive lead which is connected to the ultrasonic system through a cable 153. The numbers in each element location indicate individual channel or element number.

FIG. 6A is a plan view of the transducer array of FIG. 5 illustrating operation thereof in a sector scan application similar to that employed in a phased array sector scanning system. The element numbers in FIG. 6A now indicate common timing for both transmit and receive. By way of example, by transmitting on channels with number 1 first and thence on channels with number 2 after a specific fixed time delay τ and thence on the remainder in a similar manner with similar time delay will cause the acoustic beam to be steered in a direction other than normal to the surface. FIG. 6B depicts a cross section of the transducer array 161 normal to the cylindrical axis 162 and displays the transmitted beam 163 offset from the cylindrical axis. The wave front 164 generated by superposition of Huygens wavelets is shown. Similar time delays would be employed to receive acoustic energy preferentially only from the same direction as the transmitted beam. Thus, by energizing rows of transducer elements with variable time delays between rows the anatomical structure of a patient under examination can be scanned and an area of interest such as a blood vessel can be localized.

After location of the blood vessel of interest, the array of transducer elements may be switched to operate as a near-field Doppler transducer as sketched in FIG. 3. All of the discrete elements are now organized into either a central disc group as identified by number 1 in FIG. 7A or the annular element group as identified by number 2. Figure 7B shows a cross sectional view of the array 171, the narrow beam 172 and the wide beam 173 which covers the entire cross sectional vessel lumen area. The organization into group 1 or group 2 implies that all elements transmit simultaneously with no interelement time delay. They also all receive simultaneously, with the central elements partitioned off to allow calculation of the Doppler power spectrum.

In the far-field application, all elements of the array are partitioned off according to their distance from the center of the array, as sketched in FIG. 8. The array then approximates a plurality of concentric annular rings, similar in operation as the annular array described by Dietz et al in "Expanded Aperture Annular Array", *Ultrasonic Imaging,* Vol. 1, 1979, pgs. 56–75. Each of the groups of transducer elements 1–12 approximate an annular ring element. To achieve a broad beam, "annular rings" and "central disc" represented by numbers 1 through 3 only, for example, may be used while a larger number of "annular rings" may be used to focus on a central spot in the middle of the vessel.

As per Dietz et al, for increased focal length of the transducer array more annular rings are energized with the fartherest focal length being realized by energizing all elements of the transducer array in sequence as illustrated in FIG. 8. In this illustration twelve annular transducers are approximated by energizing the elements in sequence from 12 to 1.

By so employing a two dimensional array of transducer elements, the modes of sector scan and Doppler flow measurement are realized and a widely variable field of focus is accommodated. While the application has been illustrated with reference to a transducer array having a limited number of transducer elements, it will be appreciated that improved fidelity is realized by using an increased number of elements, and an increased field of focus is realized by expanding the size of the total array.

Thus, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In a method of measuring blood flow in a vessel by Doppler techniques, the steps of:
   providing a two dimensional transducer array including a plurality of discrete transducer elements in a generally planar pattern, each transducer element being electrically and acoustically separated from other transducer elements, and each of said transducer elements being selectively actuated,
   selectively actuating said transducer elements in a first modality as a linear transducer array for sector scanning and locating a vessel of interest,
   selectively actuating said transducer elements in a second modality as a plurality of annular arrays for far field focusing on said vessel for blood flow measurements, and
   selectively actuating said transducer elements in a third modality as a central disc and an outer annulus for near field focusing on said vessel for blood flow measurements.

* * * * *